US011344363B2

United States Patent
Ko et al.

(10) Patent No.: US 11,344,363 B2
(45) Date of Patent: May 31, 2022

(54) RF TREATMENT APPARATUS INCLUDING MICRO NEEDLES, METHOD OF CONTROLLING SAME AND TREATMENT METHOD USING SAME

(71) Applicant: LUTRONIC CORPORATION, Goyang (KR)

(72) Inventors: Kwang Chon Ko, Paju (KR); Richard Howard Cohen, San Rafael, CA (US)

(73) Assignee: LUTRONIC CORPORATION, Goyang (KR)

(*) Notice: Subject to any disclaimer, the term of this patent is extended or adjusted under 35 U.S.C. 154(b) by 773 days.

(21) Appl. No.: 16/070,147

(22) PCT Filed: May 24, 2018

(86) PCT No.: PCT/KR2018/005862
§ 371 (c)(1),
(2) Date: Jul. 13, 2018

(87) PCT Pub. No.: WO2018/236059
PCT Pub. Date: Dec. 27, 2018

(65) Prior Publication Data
US 2021/0205005 A1    Jul. 8, 2021

(30) Foreign Application Priority Data
Jun. 23, 2017    (KR) .................. 10-2017-0079805

(51) Int. Cl.
*A61B 18/14*    (2006.01)
*A61B 18/12*    (2006.01)
*A61B 18/00*    (2006.01)

(52) U.S. Cl.
CPC ...... *A61B 18/1477* (2013.01); *A61B 18/1206* (2013.01); *A61B 2018/0072* (2013.01);
(Continued)

(58) Field of Classification Search
CPC ............ A61B 18/1477; A61B 18/1206; A61B 18/1492; A61B 18/14; A61B 2018/00577;
(Continued)

(56) References Cited

U.S. PATENT DOCUMENTS

| 5,472,441 A | 12/1995 | Edwards et al. |
| 5,536,267 A * | 7/1996 | Edwards ............ A61B 18/1477 604/22 |

(Continued)

FOREIGN PATENT DOCUMENTS

| KR | 10-2010-0096124 A | 9/2010 |
| KR | 20120119249 A | 10/2012 |

(Continued)

OTHER PUBLICATIONS

International Search Report for PCT/KR2018/005862 dated Sep. 7, 2018.

*Primary Examiner* — Michael F Peffley

(57) ABSTRACT

The present invention relates to an RF treatment apparatus including micro needles, a method of controlling the same, and a treatment method using the same according to the present invention have effects in that they can prevent damage to a tissue and perform optimized treatment because RF energy can be adjusted and applied based on a current-carrying area that belongs to a portion of the micro needles and that has been inserted into a tissue.

12 Claims, 17 Drawing Sheets

(52) U.S. Cl.
CPC ............... *A61B 2018/00922* (2013.01); *A61B 2018/143* (2013.01)

(58) Field of Classification Search
CPC .. A61B 2018/1425; A61B 2018/00613; A61B 2018/1475; A61B 2018/00791; A61B 2018/143; A61B 2018/00547; A61B 2018/0016; A61B 2018/126; A61B 2018/00738; A61B 2018/00779; A61B 2018/00107; A61B 2018/00452
See application file for complete search history.

(56) References Cited

U.S. PATENT DOCUMENTS

| | | | | |
|---|---|---|---|---|
| 5,868,740 | A * | 2/1999 | LeVeen | A61B 18/1477 606/41 |
| 6,165,169 | A * | 12/2000 | Panescu | A61B 18/1492 606/1 |
| 6,530,922 | B2 * | 3/2003 | Cosman | A61B 18/14 606/32 |
| 6,783,523 | B2 * | 8/2004 | Qin | A61B 18/00 606/1 |
| 6,869,430 | B2 * | 3/2005 | Balbierz | A61B 18/1477 606/41 |
| 6,962,587 | B2 * | 11/2005 | Johnson | A61B 18/1477 128/898 |
| 7,115,124 | B1 * | 10/2006 | Xiao | A61B 18/1477 606/41 |
| 7,824,394 | B2 | 11/2010 | Manstein | |
| 10,888,372 | B2 * | 1/2021 | Lu | A61B 18/1477 |
| 2002/0120261 | A1 * | 8/2002 | Morris | A61M 25/1002 606/41 |
| 2009/0112205 | A1 | 4/2009 | McGill et al. | |
| 2012/0303015 | A1 * | 11/2012 | Shin | A61B 18/1477 606/33 |
| 2014/0194789 | A1 * | 7/2014 | Ko | A61B 5/6848 601/18 |

FOREIGN PATENT DOCUMENTS

| | | |
|---|---|---|
| KR | 10-2012-0126706 A | 11/2012 |
| KR | 10-2013-0012805 A | 2/2013 |
| WO | WO2012144712 A1 | 10/2012 |
| WO | 2012153927 A2 | 11/2012 |

* cited by examiner

RF TREATMENT APPARATUS INCLUDING MICRO NEEDLES, METHOD OF CONTROLLING SAME AND TREATMENT METHOD USING SAME

CROSS REFERENCE TO RELATED APPLICATIONS PARAGRAPH

This application is a U.S. National Stage of PCT/KR2018/005862, filed May 24, 2018, which claims the priority benefit of Korean Patent Application No. 10-2017-0079805, filed on Jun. 23, 2017 in the Korean intellectual property office, the disclosures of which are incorporated herein by reference.

TECHNICAL FIELD

The present invention relates to an RF treatment apparatus including micro needles, a method of controlling the same, and a treatment method using the same and, more particularly, to a treatment apparatus for treating a tissue by controlling energy according to the insulating units of micro needles inserted into the skin, a method of controlling the same and a treatment method using the same.

BACKGROUND ART

A method of treating a tissue may be divided into a method of treating a tissue outside the tissue and an invasive treatment method of treating a tissue by inserting some of or the entire treatment apparatus into the tissue. The invasive treatment method basically uses a treatment apparatus having a thin-necked insertion unit, such as a needles or a catheter. Treatment is performed after the treatment apparatus is inserted into a target location within a tissue.

The invasive treatment method includes various treatment behaviors, such as delivering a treating substance to the inside of a tissue, performing surgical treatment through a mechanical operation in the state in which a specific tissue within a tissue is adjacent, or delivering energy to a target location within a tissue. The treatment method has been disclosed in Korean Patent Application Publication No. 10-2011-0000790, and is applied in various methods.

Meanwhile, the current-carrying area of micro needles need to be different for various reasons, such as treatment purposes and individual variations, but a conventional technology does not disclose a technology for satisfying such needs.

DISCLOSURE

Technical Problem

An object of the present invention is to provide a treatment apparatus using RF energy, which is capable of treatment optimized for a treatment purpose and each individual by changing the current-carrying areas of micro needles inserted into a tissue, a method of controlling the same and a treatment method using the same.

Technical Solution

As means for solving the object, there may be provided a treatment apparatus using RF energy, including a main body, an RF generator provided in the main body and configured to generate RF energy, a handpiece held and used by a user and configured to receiving the RF energy and transfer the RF energy to a target tissue, a tip provided at the end of the handpiece and comprising a micro needle configured to be inserted into the target tissue, and a controller configured to control the applied RF energy based on the current-carrying area of the micro needle, a method of controlling the same, and a treatment method using an RF.

In this case, the treatment apparatus may further include an insulating unit configured to insulate part of an external surface of the micro needle.

Meanwhile, the insulating unit may be provided at plurality of points spaced apart at specific intervals in the length direction of the micro needles so that the current-carrying area of the micro needles is formed in plural.

Furthermore, power or application time of the RF energy may be controlled to be increased when the current-carrying area is widened.

In this case, the insulating unit may be configured to surround the micro needles and slide in a length direction so that the current-carrying area is controlled.

Meanwhile, the treatment apparatus may further include an insulating unit driving unit moving the insulating unit in the length direction so that the current-carrying area is controlled.

Furthermore, the tip includes a plurality of micro needles, and the insulating unit may be provided in each of the micro needles.

Moreover, the insulating unit driving unit may be configured to control the current-carrying areas of the plurality of micro needles identically simultaneously.

Furthermore, the insulating unit driving unit may independently change the location of each insulating unit so that the current-carrying area of each micro needles is differently configured.

Meanwhile, the controller may be configured to control the insulating unit driving unit and configured to control the RF energy based on an amount of driving of the insulating unit.

Furthermore, the tip is configured in plural, and each tip may have a different current-carrying area.

Meanwhile, each tip may include an identification unit according to the current-carrying area. The handpiece may further include an identification sensor recognizing the identification unit so that the size of the current-carrying area is determined when the tip is coupled to the handpiece.

Moreover, the controller may receive information of the identification unit from the identification sensor and control power or duration of the RF energy based on the information of the identification unit.

Meanwhile, the current-carrying area may be within 2 mm from the end of the micro needle.

In addition, there may be provided a method of controlling an RF treatment apparatus, including the steps of inserting a micro needle into a tissue, determining a current-carrying area of the micro needle, and controlling RF energy applied to the micro needles based on the current-carrying area.

In this case, the method may further include the step of controlling the current-carrying area of the micro needle.

Moreover, the step of controlling the current-carrying area may be performed by controlling an insulating area by an insulating unit provided on an external surface of the micro needle.

Meanwhile, the method may further include steps of selecting any one of a plurality of tips including micro needles having different current-carrying areas and identifying the current-carrying area.

In addition, there may be provided a tissue treatment method using an RF, including the steps of inserting a micro needle into a tissue, determining a current-carrying area of the micro needle, and controlling RF energy applied to the micro needles based on the current-carrying area.

In this case, the tissue treatment method may further include the step of controlling the current-carrying area of the micro needle.

Furthermore, the tissue treatment method may further include the steps of selecting any one of a plurality of tips including the micro needles having different current-carrying areas and identifying the current-carrying area.

Advantageous Effects

The RF treatment apparatus including micro needles, the method of controlling the same, and the treatment method using the same according to the present invention have effects in that they can prevent damage to a tissue and perform optimized treatment because they can apply RF energy by controlling the RF energy based on the current-carrying area of a portion of a micro needle inserted into a tissue.

MODE FOR INVENTION

Figure 1:
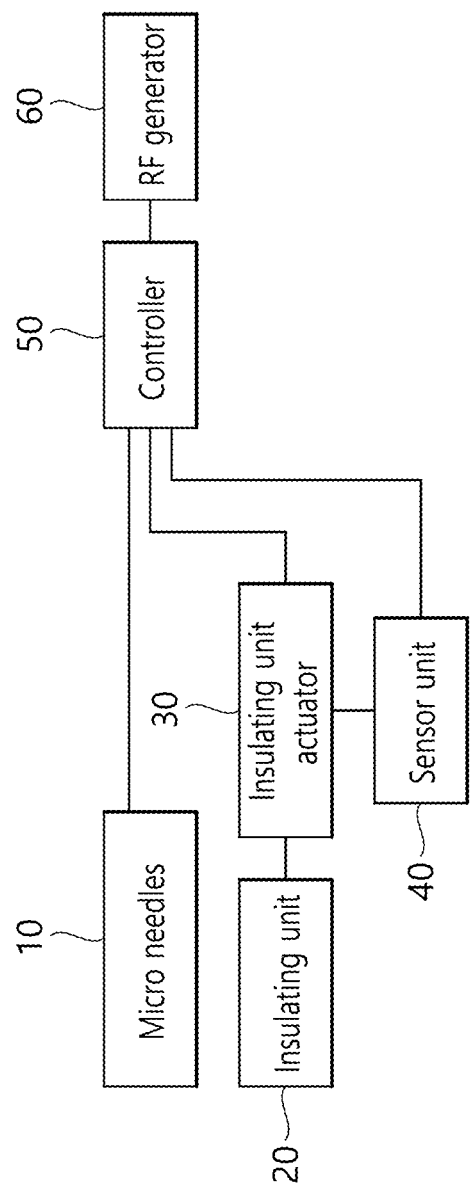
FIG. 1 is a block diagram for the concept of a first embodiment of the present invention.

Hereinafter, an RF treatment apparatus including micro needles, a method of controlling the same, and a treatment method using the same according to embodiments of the present invention are described in detail with reference to the accompanying drawings. Furthermore, in the following description of the embodiments, elements may be named differently in the field to which the present invention pertains. However, if the elements have functional similarity and identity, they may be considered to be equivalent elements although they adopt modified embodiments. Furthermore, reference numerals assigned to respective elements are written for convenience of description. However, contents shown in the drawings in which the reference numerals are written do not restrict respective elements to the ranges in the drawings. Likewise, although the elements in the drawings adopt partially modified embodiments, they may be considered to be equivalent elements if the elements have functional similarity and identity. Furthermore, a description of an element is omitted if the element is recognized as being an element that must be naturally included in view of the level of a person having ordinary skill in the art.

A first embodiment according to the present invention is described in detail below with reference to FIGS. 1 to 9.

Figure 2:
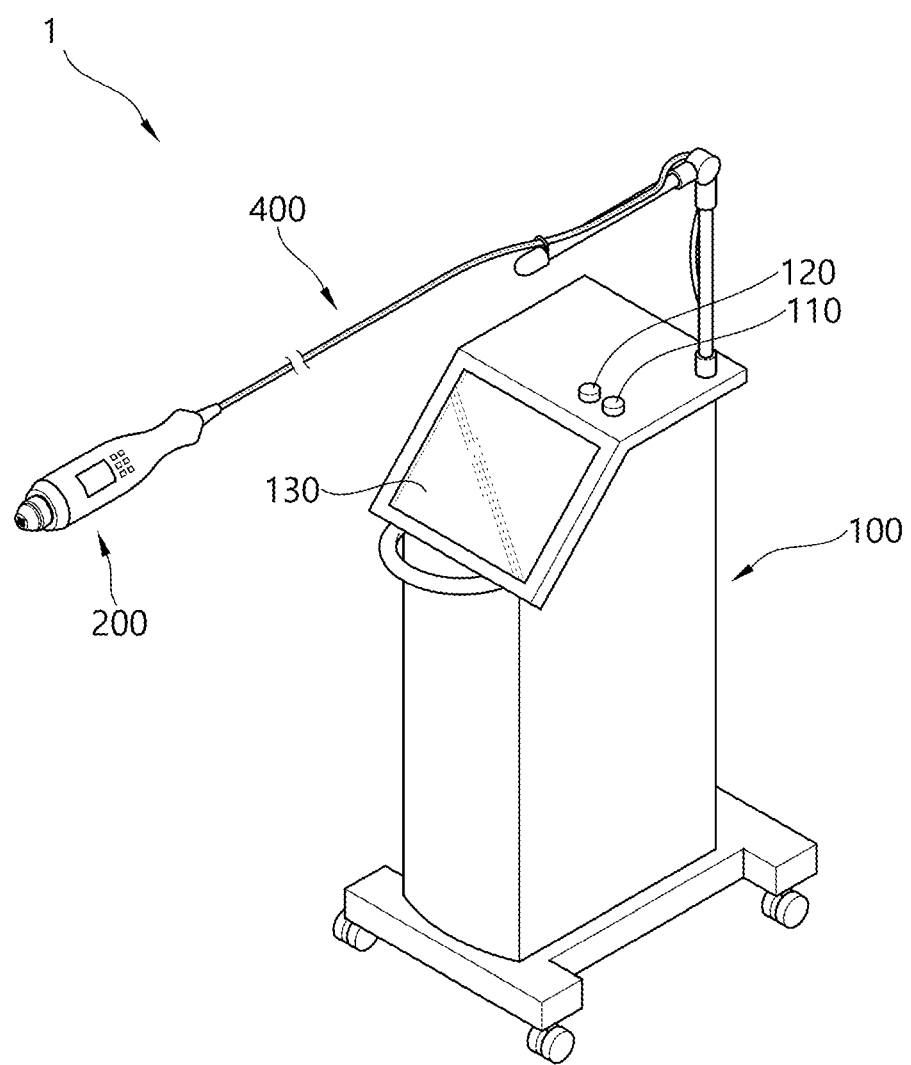
FIG. 2 is a perspective view of the first embodiment.
Figure 3:
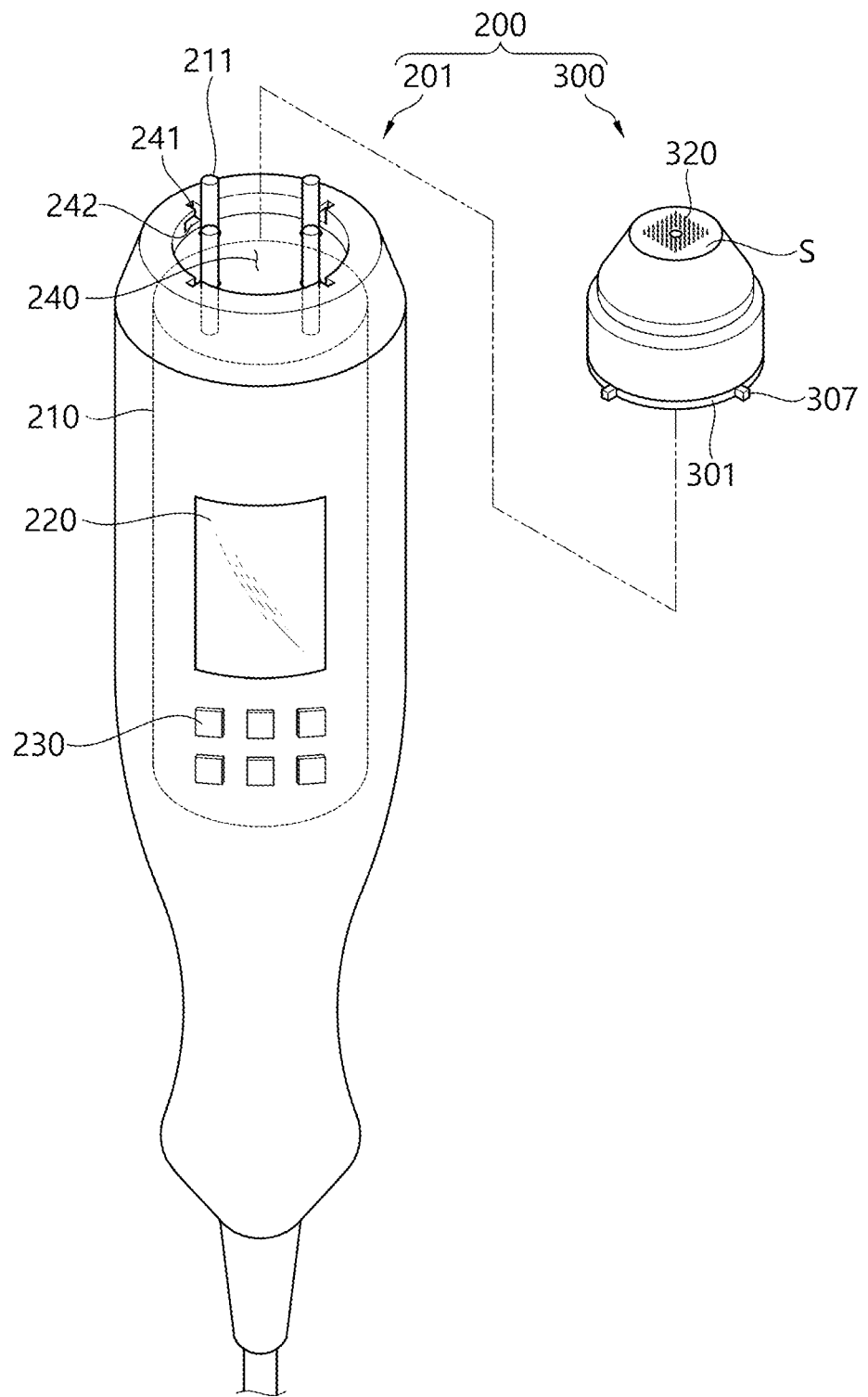
FIG. 3 is a perspective view showing a handpiece of the first embodiment.

FIG. 1 is a block diagram for the concept of the first embodiment of the present invention. FIG. 2 is a perspective view of the first embodiment. FIG. 3 is a perspective view showing a handpiece of the first embodiment.

A treatment apparatus 1 according to the present embodiment is an apparatus in which an insertion unit is inserted into a skin tissue of the human body to transfer energy to the skin tissue. The insertion unit of the present embodiment includes a plurality of micro needles, and may transfer energy to the inside of a skin tissue through the ends of the needles. Specifically, the treatment apparatus according to the present embodiment includes a main body 100, a handpiece 200 that a user can grasp and perform treatment, and a connection unit 400 connecting the main body and the handpiece.

An RF generator 60 and a controller may be provided within the main body 100. The RF generator is an element corresponding to the treatment operating unit of the present invention, and generates RF energy used for treatment. The frequency of the RF energy generated by the RF generator may be controlled depending on a patient's physical constitution, treatment purposes, a treatment portion, etc.

Furthermore, the frequency of the RF energy may be controlled in accordance with the current-carrying area of micro needles determined based on the location of an insulating unit to be described later. For example, RF energy used for skin treatment may be controlled in the range of 0.1 to 10 MHz.

The controller functions to control RF energy in response to a user's input and a plurality of sensing values and to control various operation, such as the driving of the handpiece. Meanwhile, a core function of the controller is described in detail below.

An on/off switch 110 of power, a frequency control lever 120 capable of controlling the frequency of RF energy generated by the RF generator, and a touch screen 130 on which a variety of types of information including operating contents of the treatment apparatus are displayed and treatment information is displayed and in which a user can input a command may be positioned on an external surface of the main body 100.

Meanwhile, the handpiece 200 is connected to the main body by the connection unit 400. The connection unit 400 may transfer RF energy, generated by the RF generator of the main body, to a plurality of needles 320 corresponding to the insertion unit of the present invention, and may transfer power from the main body, which is necessary for various elements on the handpiece side to operate. The connection unit 400 is configured in a cable form and may use a cable including a plurality of metal lines covered with insulating coating.

A needles driving unit 210, an insulating unit driving unit, and a sensor unit are positioned within the handpiece 200. The needles driving unit 210 is configured to linearly move output terminals 211 provided at the end of the driving unit in the length direction. As the output terminals 211 are linearly moved, the plurality of needles 320 disposed at the end of the output terminals may appear and disappear to the outside of a contact surface of the handpiece. Accordingly, the plurality of needles 320 may be inserted into a patient's tissue or drawn out from the tissue by the driving of the needles driving unit 210. The needles driving unit 210 may be formed of a linear actuator using a solenoid or a hydraulic/pneumatic cylinder. Furthermore, the insulating unit driving unit for driving the insulating unit may be provided within the handpiece 200. The insulating unit driving unit may be configured to have a construction similar to that of the needles driving unit and to linearly move the insulating unit in the length direction of the needles. The sensor unit is configured to measure a linear moving distance according to the driving of the insulating unit driving unit.

A handpiece manipulation unit 230 and a handpiece display unit 220 may be provided on an external surface of the handpiece 200. The handpiece manipulation unit 230 is configured to manipulate the on/off of the handpiece, control the insertion depth of the insertion unit 10 or control the amount of energy transferred through the insertion unit 10. The handpiece display unit 220 may display a variety of types of information for a user during a setting mode or treatment. Accordingly, the user can easily control treatment contents during treatment through the handpiece manipulation unit 230 in the state in which the user has grasped the handpiece, and can easily check treatment contents through the handpiece display unit 220.

A tip module 300 is provided at the end of the handpiece. The tip module includes the plurality of needles 320 and may be detachably positioned in the main body 201 of the handpiece. Specifically, a base 301 forms the bottom of the tip module. Outward protruded detachment protrusions 307 are formed in the outside wall of the base. Guide grooves 241 guiding the detachment protrusions and anti-separation grooves 242 for preventing the detachment of the detachment protrusions 307 guided along the guide grooves 241 are formed in a recess part 240 to which the tip module is coupled on the handpiece side. Furthermore, the detachment protrusions 307 of the tip module are installed on the handpiece in such a manner that they are guided along the guide grooves 241 and coupled to the anti-separation grooves 242. In this case, as in the present embodiment, what the tip module is detachably installed on the handpiece is an example, and the tip module may be integrated with the handpiece.

Figure 4A:
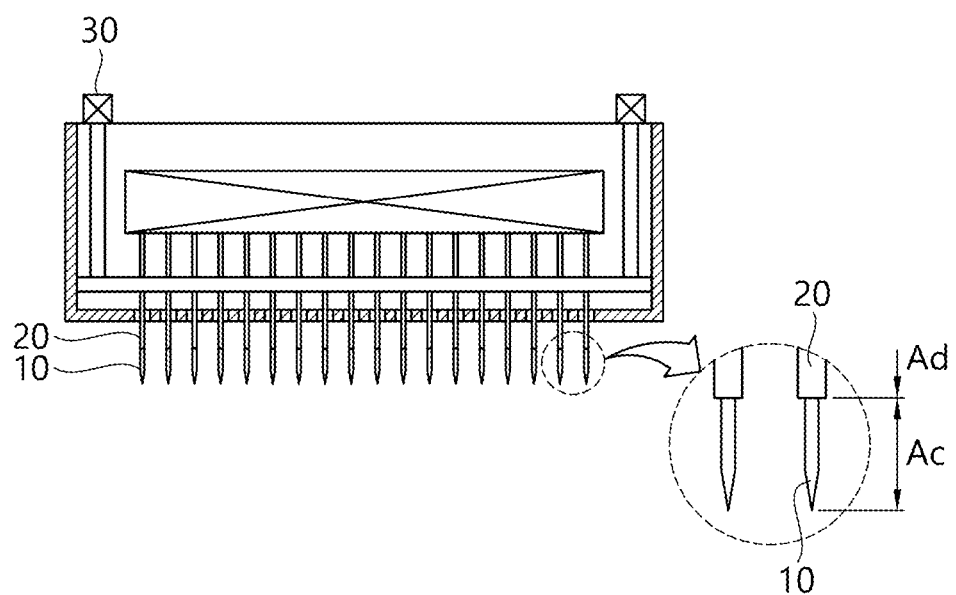
FIGS. 4a and 4b are diagrams showing control of a current-carrying area of the first embodiment.
Figure 4B:
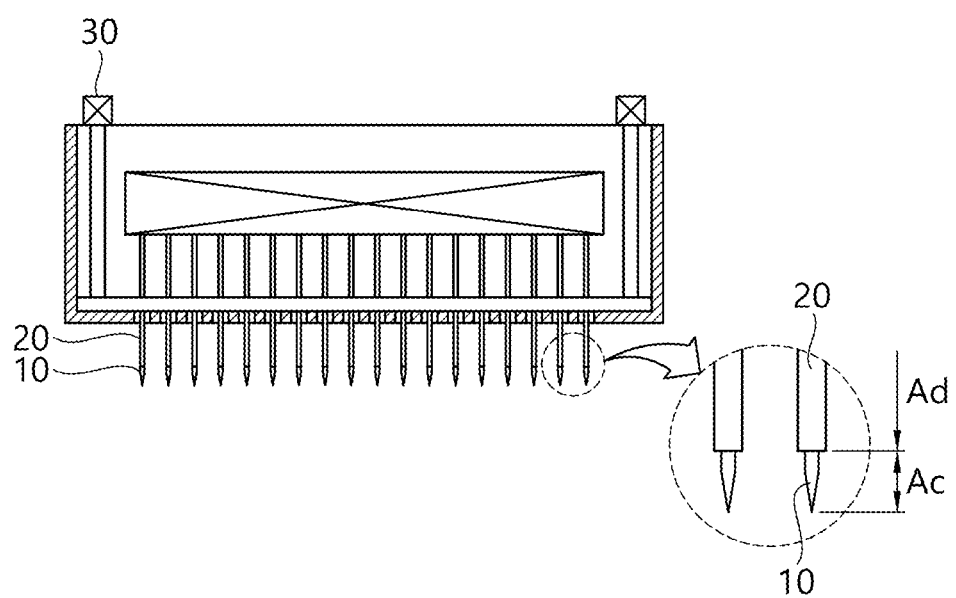

FIGS. 4a and 4b are diagrams showing control of a current-carrying area Ac of the first embodiment. FIG. 4a shows the state in which the length of a portion that belongs to the micro needles and that has not been insulated has been increased and thus a current-carrying area Ac has been increased. FIG. 4b shows the state in which the length of a portion that belongs to the micro needles and that has not been insulated has been decreased compared to FIG. 4a and thus the current-carrying area Ac has been reduced. As shown, an array of the micro needles 10 is provided within the tip 300. The insulating unit 20 extended in the length direction and configured to relatively slide with respect to the micro needles is provided in the circumference of each micro needles 10. The external area of the micro needles 10 is divided into the current-carrying area Ac, that is, a first region, and an insulating area Ad, that is, a second region, by the insulating unit 20. The insulating unit 20 is configured to prevent RF energy from being applied near the micro needles 10. A hollow may be formed within the insulating unit in the length direction so that the micro needles 10 can pass through the insulating unit. The insulating unit 20 may be inserted into a tissue along with the micro needles 10 in the state in which it has surrounded part of the micro needles 10. Meanwhile, a plurality of the insulating units 20 may be fixed to a single frame so that all the insulating units 20 can slide at the same time. In this case, the frame may be supported by the insulating unit driving unit 30 to advance or retreat. In this case, the insulating unit driving unit 30 may control the location of the insulating units 20 so that the moving distance of only some of the plurality of needles is controlled identically or individually.

The insulating area Ad is an area insulated by the insulating unit 20. The current-carrying area Ac is an area where the insulating unit 20 is not positioned and that is exposed to the outside. The current-carrying area Ac is formed in a specific length from the end of the micro needles 10. In this case, the current-carrying area Ac may be determined based on a depth into a tissue. Specifically, if the treatment apparatus is applied to the skin, the current-carrying area Ac may be determined within 2 mm from the end of the micro needles 10.

The insulating unit 20 is configured to slide along the micro needles and advance and retreat in the length direction by the insulating unit driving unit 30. As the insulating unit 20 advances and retreats, the externally exposed current-carrying area Ac of the micro needles 10 is determined.

Figure 5:
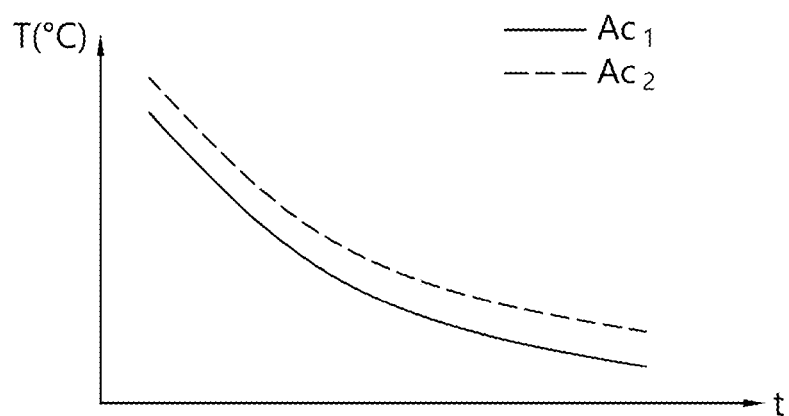
FIG. 5 is a graph showing a temperature of a tissue over time when RF energy is applied.

FIG. 5 is a graph showing a temperature of a tissue over time when RF energy is applied. FIG. 5 shows results in which the temperature of the tissue rises in reverse proportion to an application time when the same RF energy is applied. In this case, although the same energy is applied for the same time, a change in the temperature is different depending on the current-carrying area Ac of the micro needles 10. Specifically, when energy is applied, it is absorbed around the current-carrying area Ac of the micro needles 10. The area where the energy is absorbed is different depending on the current-carrying area Ac. For example, specifically, if a first current-carrying area Ac1>a second current-carrying area Ac2 is set and the same energy is applied with the same power, when the first current-carrying area Ac is set to be wider and energy is applied, a temperature rise is slightly reduced. The reason for this is that a corresponding rate of rise is slowed down because the same energy is absorbed by a greater volume as described above.

Figure 6:
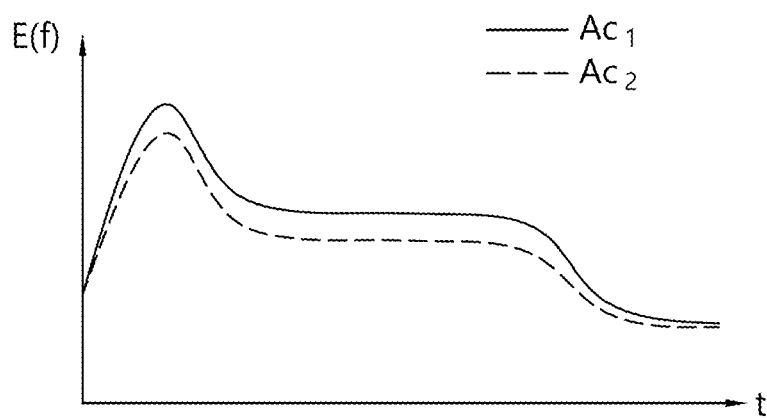
FIG. 6 is a graph showing energy application when two current-carrying areas are applied.

FIG. 6 is a graph showing the application of energy when the two current-carrying areas Ac are applied. High energy is applied when RF energy is applied. Accordingly, it is preferred to maximize a treatment area while preventing the excessive destruction of a tissue. In particular, if a treatment area is to be limited, for example, if treatment needs to be performed only in a specific depth or less from a skin surface, the thickness of a tissue may be different for each part when a large area is treated while moving on the skin surface. In this case, excessive damage may occur in a portion in which the tissue is thin or impedance is high although energy of the same power is applied.

Accordingly, the controller 50 controls RF energy in accordance with a change in the current-carrying area Ac.

As described above, the current-carrying area Ac is illustrated as having the first current-carrying area Ac1>the second current-carrying area Ac2. Referring to the energy application graph, when RF energy is applied, energy of peak power is initially transferred to minimize the treatment time, and power of a proper level is applied for a specific time. If the tissue is determined to have reached a treatment temperature, there occurs a phase in which the RF power is reduced and remains intact in order to maintain the treatment temperature. In this case, if the current-carrying area Ac of the electrode is reduced, the temperature rises more rapidly because the volume of the tissue that absorbs the same energy is reduced. Accordingly, the controller 50 may generally reduce and apply the RF power in order to secure a similar treatment volume. In this case, the variation tendency may occur regardless of the varying volume. That is, the controller 50 applies the RF energy based on programmed contents. In this case, the controller controls the RF power based on the current-carrying area Ac of the micro needles 10 and applies the controlled RF power. In this case, the RF power is controlled during the entire energy application phase because the current-carrying area Ac of the micro needles 10 is first determined before the RF energy is applied.

Figure 7:
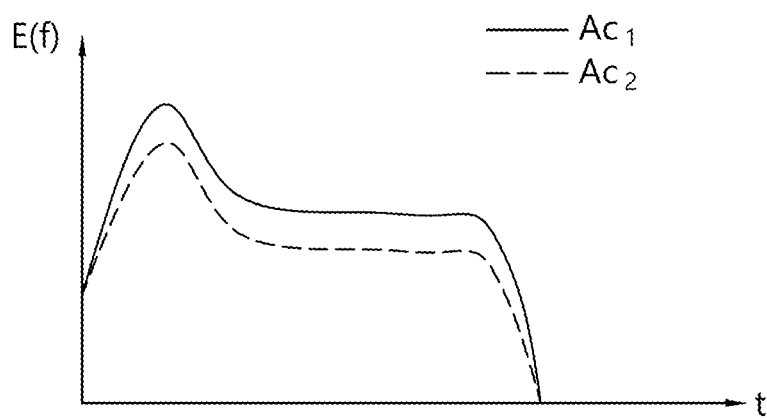
FIG. 7 is a graph showing anther energy application when the two current-carrying areas are applied.

FIG. 7 is a graph showing anther energy application when the two current-carrying areas Ac are applied. Unlike the example described with reference to FIG. 5, this drawing shows RF energy according to time when RF energy is cut off when a treatment temperature is reached. In this case, as described above, the current-carrying area Ac of the micro needles 10 is first determined before the RF energy is applied. Accordingly, RF power is determined based on the determined current-carrying area Ac, and the RF energy is applied. This drawing shows that the RF power applied to Ac2 tends to be slightly reduced if the current-carrying area Ac is small.

Figure 8A:
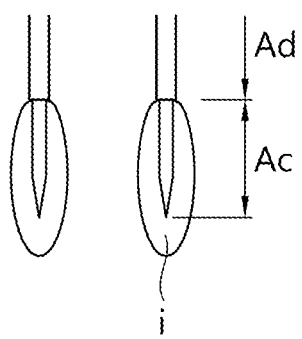
FIGS. 8a, 8b and 8c show the state in which the first embodiment is used.
Figure 8B:
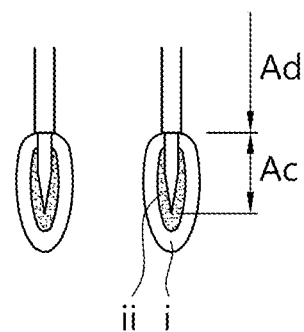
Figure 8C:
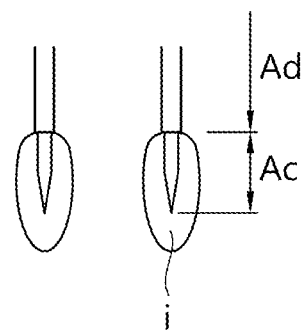

FIGS. 8a, 8b and 8c show the state in which the first embodiment is used. FIGS. 8(a) and 8(b) show a case where RF energy of the same power is applied, but the current-carrying areas Ac are different. Furthermore, FIGS. 8(b) and 8(c) show the state of a tissue when the same current-carrying area Ac or RF energy is controlled.

When the RF energy is applied to the skin tissue, a temperature rises and the tissue starts to denature in the temperature range of 40 to 80° C. At this time, the state of the tissue may be a coagulation state (i). Thereafter, when the temperature further rises, the state of the tissue becomes an ablation state (ii). In general, it has been known that in an operation for beauty treatment, such as the retightening of a tissue, a skin tissue is denaturized into the coagulation state and the operation is performed. In this case, the occurrence of ablation is not preferred.

Referring back to FIG. 8a, when compared to FIGS. 8b and 8c, the current-carrying area Ac is FIG. 8a>FIG. 8b=FIG. 8c. In the case of FIG. 8a having a wide current-carrying area Ac, when the same RF energy is applied, the amount of coagulation occurred is generally increased. Meanwhile, in FIG. 8b having a small current-carrying area Ac, when RF energy having the same power as that of FIG. 8a is applied, the volume that absorbs the RF energy is reduced. Accordingly, coagulation occurs although the RF energy of the same power is applied. Moreover, excessive damage the tissue occurs because ablation occurs. Accordingly, the controller 50 controls RF energy so that reduced RF power is applied based on the current-carrying area Ac depending on the location of the insulating unit 20 as in FIG. 8c in order to prevent excessive damage.

Figure 9A:
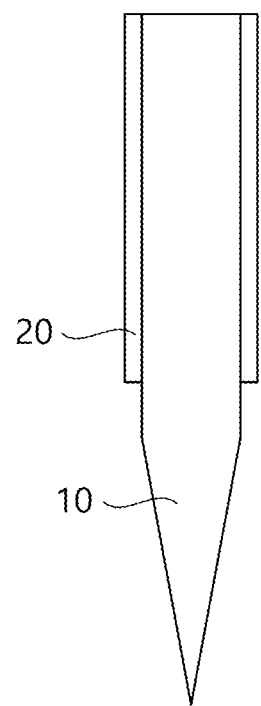
FIGS. 9a, 9b and 9c are modified examples of micro needles and insulating unit of the first embodiment.
Figure 9B:
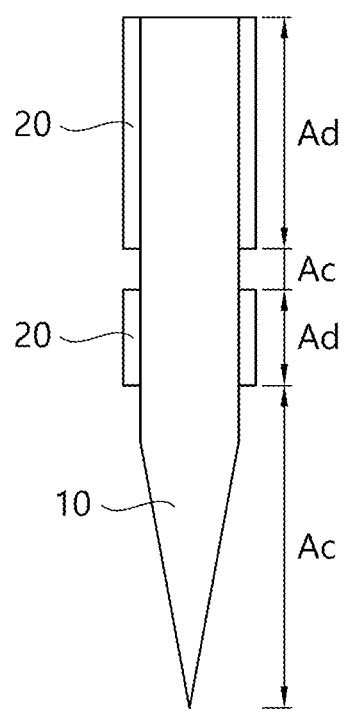
Figure 9C:
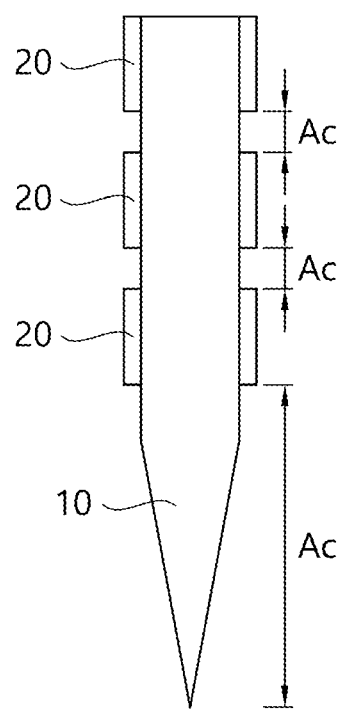

FIGS. 9a, 9b and 9c are modified examples of the micro needles and insulating unit of the first embodiment. As shown in FIG. 9a, the insulating unit 20 included in the micro needles 10 may be configured to have an insulating area continuously formed as described with reference to FIGS. 1 to 8. Meanwhile, as shown FIGS. 9b and 9c, unlike in FIG. 9a, the insulating unit may be configured to have a plurality of separated points formed therein. If an operation is performed using the micro needles 10 in which the current-carrying areas other than the insulating area have been formed in the plurality of separated points, treatment may be performed on the plurality of separated points through one invasion into a tissue. In this case, the controller 50 may control RF energy based on the sum of the current-carrying areas Ac separated in the micro needles 10.

Hereinafter, a second embodiment according to the present invention is described in detail with reference to FIG. 10. The present embodiment may be configured to include the same elements as the aforementioned embodiment. In order to avoid redundant writing, a description is omitted and a different configuration only is described.

Figure 10:
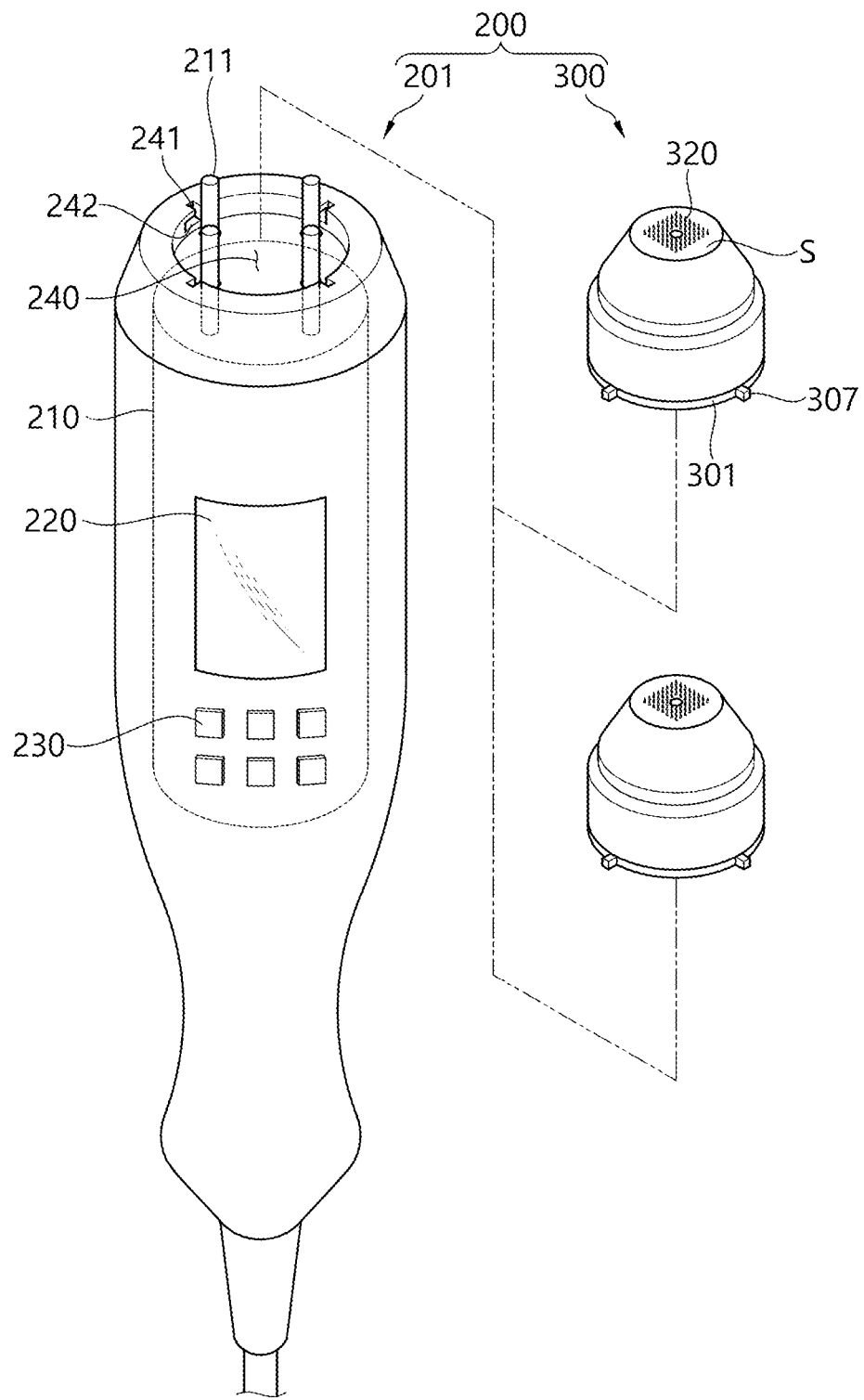
FIG. 10 is a perspective view showing a handpiece of a second embodiment.

FIG. 10 is a perspective view showing a handpiece 200 of the second embodiment. As shown, the RF treatment apparatus according to the present invention may include a plurality of tips 300 coupled to the handpiece 200.

In the plurality of tips 300, the length of the insulating unit 20 may be configured differently. The plurality of tips 300 in which the lengths of the insulating units 20 are different form a single set, and may be configured so that a user selectively selects the current-carrying area Ac of the micro needles 10.

In the present embodiment, an identification unit and an identification sensor may be provided so that the tips 300 having different current-carrying areas Ac are distinguished.

The identification unit is included in each of the plurality of tips 300. The identification unit may use various methods, such as an RFID or a marker, so that the size of the current-carrying area Ac is recognized.

Meanwhile, the identification sensor for identifying the identification unit may be provided in the handpiece 200. Accordingly, when the tip 300 is coupled to the handpiece 200, the controller 50 immediately recognizes the identification unit of the tip. The controller 50 identifies the coupled tip 300 and controls RF power or duration in accordance with the current-carrying area Ac of each tip 300.

As described above, in the RF treatment apparatus according to the present invention, the insulating unit 20 directly operates and thus the current-carrying area Ac of the micro needles 10 becomes different, or RF energy may be applied to a tissue using the plurality of tips 300 having different current-carrying areas Ac. In this case, the controller 50 can prevent excessive damage and perform optimized treatment by controlling applied RF energy based on the current-carrying area Ac.

Figure 11:
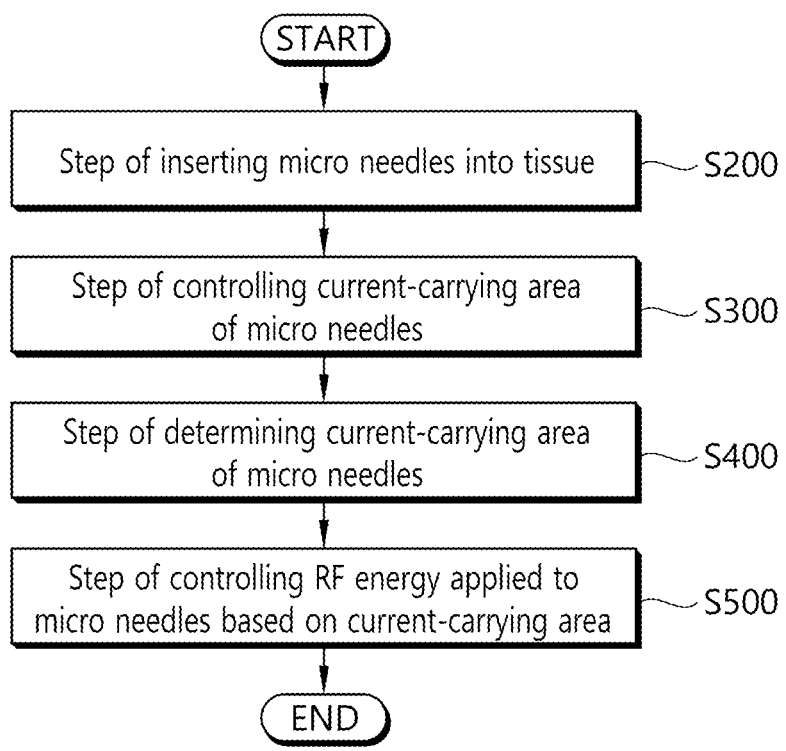
FIG. 11 is a flowchart of a method of controlling an RF treatment apparatus according to a third embodiment.

Hereinafter, a method of controlling the RF treatment apparatus according to the third embodiment of the present invention is described in detail with reference to FIG. 11.

As shown, the method of controlling an RF treatment apparatus according to the third embodiment of the present invention may include a step S200 of inserting micro needles into a tissue, a step S300 of controlling the current-carrying area of the micro needle, the step S400 of determining the current-carrying area, the step S500 of controlling RF energy.

The step S200 of inserting a micro needle into a tissue corresponds to the step of inserting a micro needle into a tissue, that is, a treatment target.

The step S300 of controlling the current-carrying area of the micro needles corresponds to the step of controlling the current-carrying area based on the state of the tissue, a treatment purpose, etc. in the state in which the micro needles has been inserted into the tissue. In this case, the insulating unit formed to surround the circumference of the micro needles may be used. The current-carrying area may be controlled by advancing or retreating the insulating unit in the length direction of the micro needle.

The step S400 of determining the current-carrying area corresponds to the step of determining whether the controlled current-carrying area is appropriate.

The step S500 of controlling the RF energy corresponds to the step of controlling RF energy based on the current-carrying area.

Figure 12:
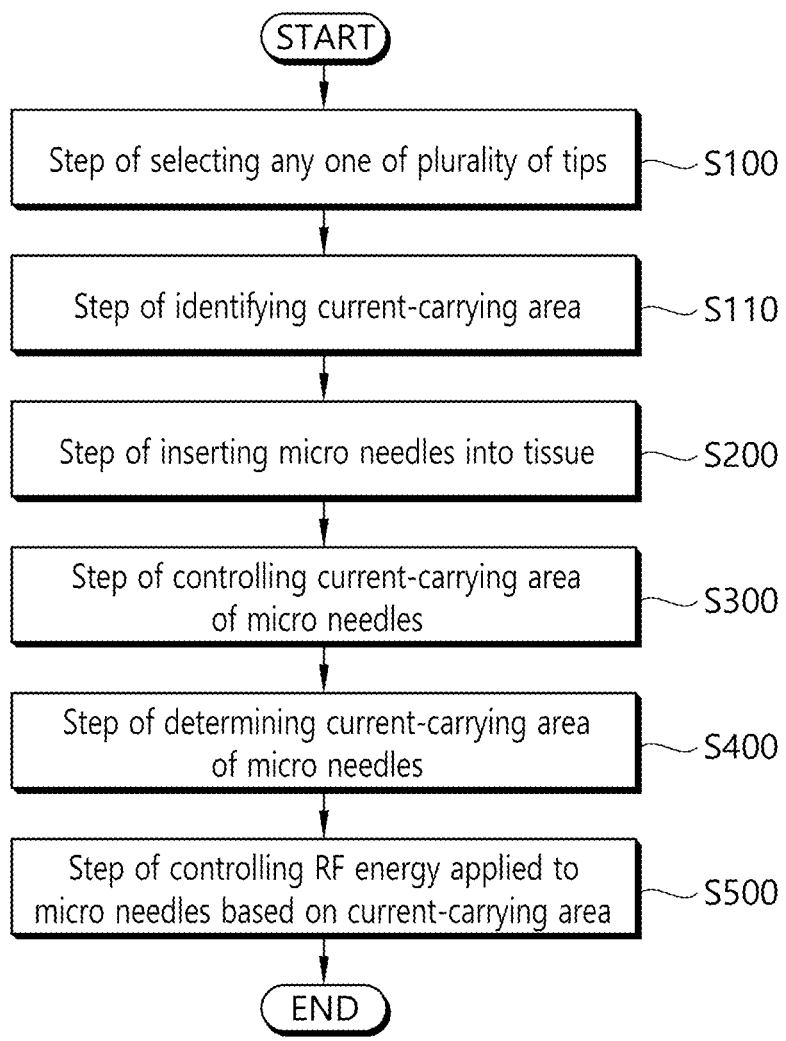
FIG. 12 is a flowchart of a treatment method using an RF treatment apparatus according to a fourth embodiment.

FIG. 12 is a flowchart of a treatment method using the RF treatment apparatus according to a fourth embodiment. As shown, the method of controlling an RF treatment apparatus according to the third embodiment of the present invention may include a step S100 of selecting any one of a plurality of tips, a step S110 of identifying a current-carrying area, a step S200 of inserting micro needles into a tissue, and a step S500 of controlling RF energy applied to the micro needles based on the current-carrying area.

The step S100 of selecting any one of a plurality of tips corresponds to the step of selecting, by a user, any one of a plurality of tips. In the plurality of tips, the current-carrying areas of micro needles are differently configured. A user may select a tip based on an operation purpose, the characteristics of a patient's tissue, etc.

The step S110 of identifying a current-carrying area corresponds to the step of identifying, by the controller, a current-carrying area when the tip is coupled to the handpiece. Meanwhile, the user may input unique code corresponding to the current-carrying area to the controller using the identification unit of the tip.

The step S200 of inserting micro needles into a tissue corresponds to the step of positioning, by the user, the handpiece in a tissue and inserting the handpiece into the tissue by advancing the micro needle. In this case, the insulating unit for insulating some of the micro needles may also be inserted into the tissue.

The step S500 of controlling RF energy applied to the micro needles based on the current-carrying area corresponds to the step of performing optimized treatment by controlling applied RF energy based on the identified current-carrying area.

The RF treatment apparatus including micro needles, the method of controlling the same, and the treatment method using the same according to the present invention have effects in that they can prevent damage to a tissue and perform optimized treatment because RF energy can be adjusted and applied based on a current-carrying area that belongs to a portion of the micro needles and that has been inserted into a tissue.

The invention claimed is:

1. A treatment apparatus using RF energy, comprising:
a main body;
an RF generator provided in the main body and configured to generate RF energy;
a handpiece configured to receive the RF energy and transfer the RF energy to a target tissue;
a tip provided at an end of the handpiece with a contact surface configured to contact the target tissue;
a plurality of micro needles provided in the tip and configured to advance through the contact surface and be inserted into the tissue;
an insulating unit provided on at least part of an outer surface of the plurality of micro needles and configured to advance through the contact surface with the micro needles;
a controller configured to control the applied RF energy based on changes to a current-carrying area of the micro needles; and
an insulating unit driving unit provided in the handpiece moving the insulating unit in the length direction so that the current-carrying area is controlled,
wherein the insulating unit surrounds the plurality of micro needles and slides along the plurality of microneedles simultaneously in a length direction by the insulating unit driving unit so that the current-carrying area is controlled.

2. The treatment apparatus of claim 1, wherein each of the plurality of microneedles has at least one insulation band that covers a circumference of the respective microneedle and is positioned distal to the insulating unit.

3. The treatment apparatus of claim 2, wherein the controller is configured to control the insulating unit driving unit and configured to control the RF energy based on an amount of driving of the insulating unit.

4. The treatment apparatus of claim 1, wherein power or an application time of the RF energy is increased in accordance with the current-carrying area when the current-carrying area is widened.

5. The treatment apparatus of claim 1, further comprising a second tip that includes a second plurality of micro needles with a different current-carrying area from the current-carrying area of the micro needles.

6. The treatment apparatus of claim 5, wherein:
each tip comprises an identification unit according to the respective current-carrying area, and
the handpiece further comprises an identification sensor recognizing the identification unit so that a size of the current-carrying area is determined when the tip is coupled to the handpiece.

7. The treatment apparatus of claim 6, wherein the controller receives information of the identification unit from the identification sensor and controls power or duration of the RF energy based on the information of the identification unit.

8. The treatment apparatus of claim 1, wherein the current-carrying area is within 2 mm from an end of the plurality of micro needles.

9. A method of controlling an RF treatment apparatus, comprising steps of:
driving an insulating unit driving unit provided in a handpiece to move an insulating unit on a plurality of micro needles so that the plurality of micro needles are modulated simultaneously;
controlling a micro needle driving unit configured to advance the plurality of micro needles with the insulating unit through a contact surface into a tissue;
determining a current-carrying area of the plurality of micro needles; and
controlling RF energy applied to the plurality of micro needles based on the determined current-carrying area.

10. The method of claim 9, further comprising steps of:
selecting any one of a plurality of tips comprising micro needles having different current-carrying areas; and
identifying the current-carrying area.

11. A tissue treatment method using RF energy, comprising steps of:
contacting a contact surface of a tip of RF treatment device to a tissue;
modulating the plurality of micro needles simultaneously by an insulating unit driving unit provided in a handpiece;
inserting a plurality of micro needles with the insulating unit provided on an outer surface of the plurality of micro needles through a contact surface of a tip into a tissue;

determining a current-carrying area of the plurality of micro needles; and controlling RF energy applied to the plurality of micro needles based on the determined current-carrying area.

12. The tissue treatment method of claim 11, further comprising steps of:

selecting any one of a plurality of tips comprising the plurality of micro needles having different current-carrying areas; and identifying the current-carrying area.

* * * * *